(12) United States Patent
Tang

(10) Patent No.: US 8,800,551 B2
(45) Date of Patent: Aug. 12, 2014

(54) DRUG DELIVERY DEVICE

(75) Inventor: James Tang, Taipei (TW)

(73) Assignee: Gold Nanotech Inc. (TW)

( * ) Notice: Subject to any disclaimer, the term of this patent is extended or adjusted under 35 U.S.C. 154(b) by 767 days.

(21) Appl. No.: 12/805,462

(22) Filed: Aug. 2, 2010

(65) Prior Publication Data

US 2011/0137281 A1 Jun. 9, 2011

(30) Foreign Application Priority Data

Dec. 3, 2009 (TW) .............................. 98141424 A

(51) Int. Cl.
| | |
|---|---|
| *A61M 11/00* | (2006.01) |
| *A61M 37/00* | (2006.01) |
| *B05B 7/04* | (2006.01) |
| *A61M 5/30* | (2006.01) |
| *B05B 7/24* | (2006.01) |
| *A61M 5/20* | (2006.01) |
| *A61M 5/24* | (2006.01) |
| *A61M 5/31* | (2006.01) |
| *B05B 17/06* | (2006.01) |

(52) U.S. Cl.
CPC ................ *A61M 5/30* (2013.01); *B05B 7/0483* (2013.01); *A61M 5/2053* (2013.01); *B05B 7/0491* (2013.01); *A61M 5/24* (2013.01); *A61M 2005/3142* (2013.01); *B05B 7/2427* (2013.01); *A61M 5/204* (2013.01); *B05B 17/06* (2013.01)
USPC ......... 128/200.21; 604/83; 604/143; 604/147

(58) Field of Classification Search
USPC ................... 604/83, 143, 140–142, 144–147; 128/200.21
See application file for complete search history.

(56) References Cited

U.S. PATENT DOCUMENTS

| | | | |
|---|---|---|---|
| 2008/0038298 A1* | 2/2008 | Barnikol-Keuten et al. | . 424/400 |
| 2008/0154183 A1* | 6/2008 | Baker et al. | ..................... 604/28 |

* cited by examiner

*Primary Examiner* — Nathan R Price

(57) ABSTRACT

A drug delivery device mainly has a housing, which can be easily held and operated. The housing has one end formed with an adjustment seat capable of adjusting a range distance, and the other end connected to a gas pressure control source for providing mainstream and substream gas pressures. Disposed in the housing are a drug delivery pressuring tube, an embedded drug-can connecting seat or an external drug-can connecting seat, a replaceable drug-can container and a gas communication tube. According to this design, the minor liquid drug can be controlled, the drug-can can be replaced and the continuous quantitative injection of drug can be made. Also, all damaged or dirty members of the invention may be disassembled, cleaned or replaced.

13 Claims, 14 Drawing Sheets

DRUG DELIVERY DEVICE

BACKGROUND OF THE INVENTION (1) Field of the Invention

The invention relates to a quantitatively controlled drug delivery device having a drug-can that can be assembled and replaced so that the continuous or single-time minor quantitative injection of the used drug can be selected.

(2) Description of the Prior Art

There are many devices for the cosmetic and medical needleless injection and microscopic treatment, and the frequently seen injector almost has a gun-shaped body having a chamber for loading the drug or other substances. The chamber is connected to a high-pressure gas. According to the high-pressure principle, the injector is pressed on the skin of the patient. When a trigger is pushed, the drug liquid is rapidly injected from a muzzle in an atomized manner.

This injector has the convenience in use and the utility, and is thus accepted by the masses. However, its structure design still has some drawbacks to be improved.

First, the power source of the injector for injecting the liquid in the atomized manner depends on the pressure of the high-pressure gas. When the external gas pressure is coupled to the injector, the adjustment has to be made manually. If the set pressure is not uniform, the spraying effect is not good. When no external gas pressure is coupled to the injector, the stability of the gas pressure control depends on the human's hand control. So, the spraying effect is not good because the applied force is not uniform.

Second, the injector usually cannot be disassembled, and the user cannot disassemble it to perform the cleaning and maintaining works. Especially, the simple failure elimination cannot be achieved by the user.

Third, the drug cannot be conveniently filled, or the drug bottle cannot be conveniently installed and replaced in some injectors, and the process is time-consuming and labor-consuming. In addition, when the drug is injected, the residual drug liquid is often left in the bottle, so that the injection amount of the drug is not precise, and the effect is naturally affected.

Fourth, the typical injector only can input the drug according to a single method set by the manufacturer, so that the flexibility and convenience in use are naturally limited.

The factors mentioned hereinabove have proved that the existing needleless injector still has to be improved.

In view of the associated problems induced by the design defects of the conventional drug delivery device, the present inventor has paid attention to the research and development according to the experience and the technology in manufacturing the associated products for many years, and thus developed this novel, convenient and utility drug delivery device to benefit the industry and the masses.

SUMMARY OF THE INVENTION

A main object of the invention is to provide a drug delivery device having the continuous quantitative injection and capable of controlling the minor liquid drug and replacing the drug-can.

Another object of the invention is to provide an assembling type drug delivery device so that the damaged or dirty members may be disassembled, cleaned or replaced.

Still another object of the invention is to provide a drug delivery device for enabling selection of the type of the injection drug-can. The embedded drug-can connecting seat is used in conjunction with the replaceable drug-can container inside the drug delivery device, and the external drug-can container is used in conjunction with the external drug-can connecting seat outside the drug delivery device. Furthermore, an ultrasonic oscillation device may be attached to the external drug-can container so that the finer spraying effect can be obtained, and the agile, convenient and diversified effects may be obtained.

The invention achieves the above-identified objects by providing a drug delivery device, which has an assembled structure and includes the units of: a housing that may be opened and closed to form an opening; an adjustment seat capable of adjusting a range distance; a drug delivery pressuring tube for pressuring and atomizing the drug; and a drug-can connecting seat for enabling selection of the type of the injected drug-can, wherein the damaged or dirty units may be disassembled and cleaned or replaced. The drug delivery device has one end formed with a fixed connection seat coupled to mainstream and substream gas pressures provided by a control source. The substream gas pressure provides the quantitative gas delivery function, while the mainstream gas pressure provides the function of pressuring and jetting the drug to inject in an atomized manner.

The working principle will be described in the following. The control source with the external supplied inert gas utilizes a proportional valve as a controller for the quantitative drug output to supply the substream gas pressure coupled to the depressuring gas communication tube in the drug delivery device through one conduit, and to supply the mainstream gas pressure coupled to the drug delivery pressuring tube in the drug delivery device via the other conduit. The drug delivery pressuring tube may be optionally assembled to an embedded drug-can connecting seat and coupled to the drug-can container in conjunction with the depressuring gas communication tube structure to obtain the continuous, stable and minor gas delivery function to push the drug liquid quantitatively. Alternatively, the externally inputted drug may be adopted, wherein an external drug-can container directly injects the drug into the external drug-can connecting seat, and the drug is inputted to the drug delivery pressuring tube for pressuring, jetting and injecting the drug in an atomized manner. Furthermore, the drug-can containers may further be provided with ultrasonic oscillation devices so that the outputted drug has the finer atomizing effect.

Further aspects, objects, and desirable features of the invention will be better understood from the detailed description and drawings that follow in which various embodiments of the disclosed invention are illustrated by way of examples.

DETAILED DESCRIPTION OF THE PREFERRED EMBODIMENTS

Figure 1:
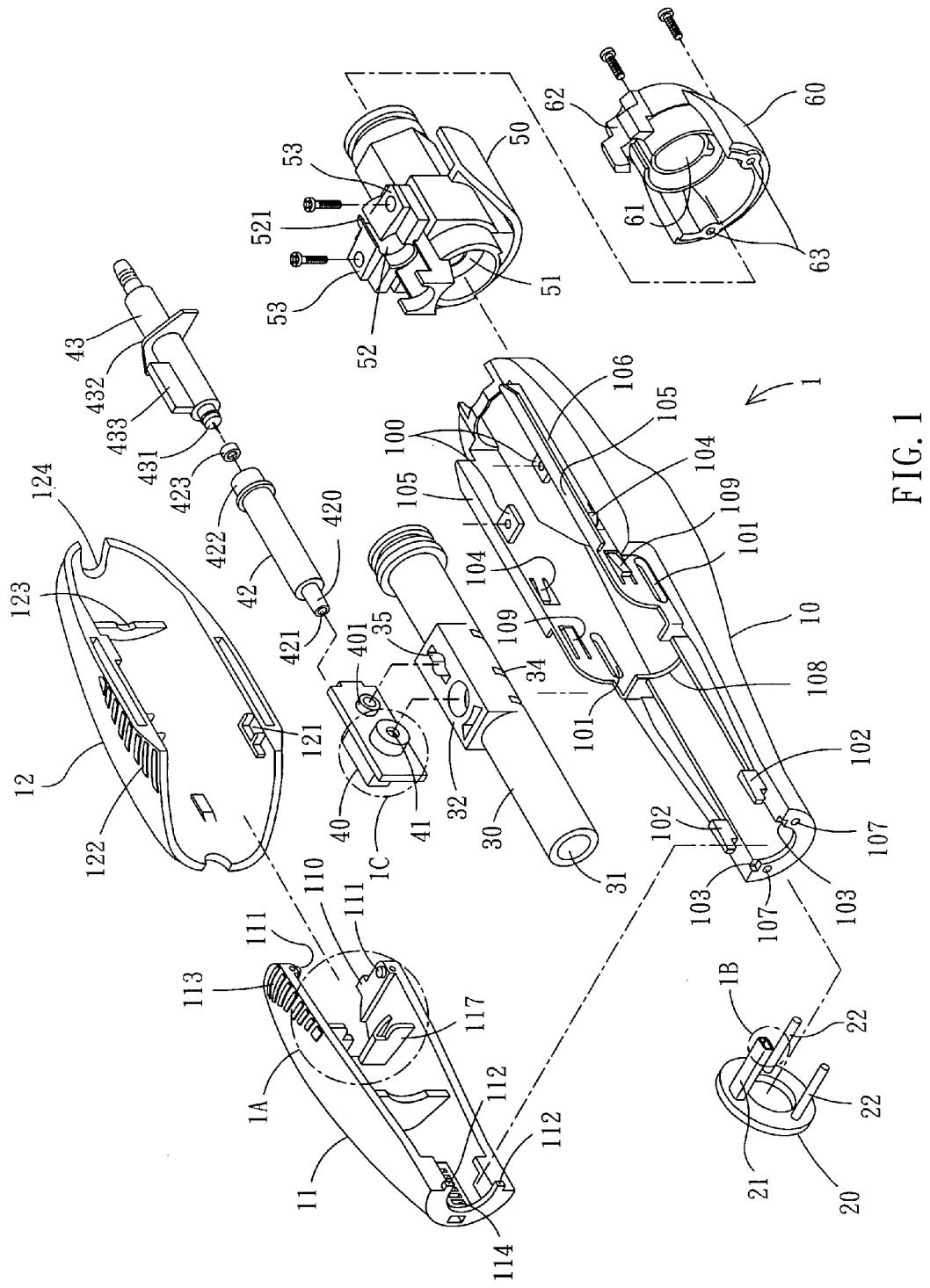
FIG. 1 is an exploded view showing a drug delivery device according to a preferred embodiment of the invention.
Figure 1C:
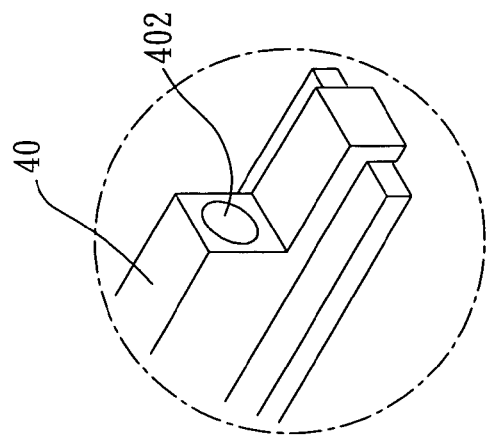
FIG. 1C is an enlarged view showing the embedded drug-can connecting seat of FIG. 1 at the other angle.
Figure 1B:
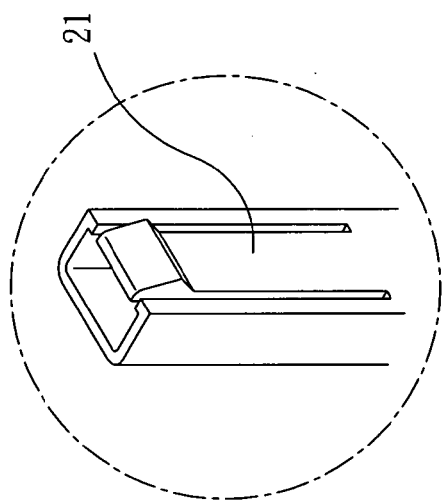
FIG. 1B is a partially enlarged view showing the elastic hook of the adjustment seat of FIG. 1.
Figure 1A:
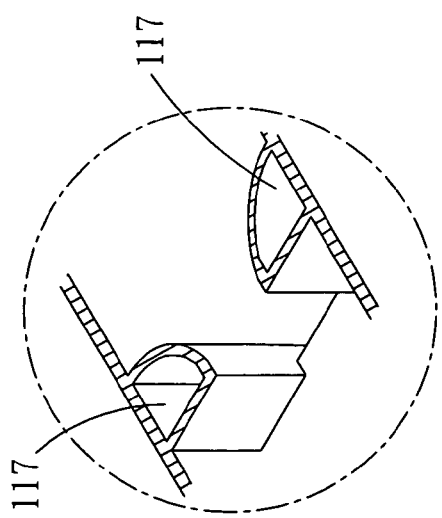
FIG. 1A is a partially enlarged view showing the base post of the front sliding cover of FIG. 1.

Referring to FIGS. 1 and 1A to 1C, a drug delivery device (1) having assembling and replaceable functions according to a preferred embodiment of the invention includes: a housing composed of a base (10), a front sliding cover (11) and a rear sliding cover (12); an adjustment seat (20) connected to a front end of the housing; a drug delivery pressuring tube (30) embedded into the base (10); an embedded drug-can connecting seat (40) connected to the drug delivery pressuring tube (30); a fixed connection seat (50) fixed to a rear end of the housing, wherein a rear mounting seat (60) is additionally screwed to the rear end of the housing. The adjustment seat (20) is in the form of a triangular insert so that a gap between the adjustment seat (20) and the housing can be adjusted. The drug delivery pressuring tube (30) is a tube body and has an inner hole (31) having gradually decreasing diameters from two ends to the middle. In addition, a middle section of an outer circumferential surface of the drug delivery pressuring tube (30) has a connection portion (32) formed with a penetrated thin channel (33) communicating with the inner hole (31) (see FIG. 4). The drug delivery pressuring tube (30) also has a positioning groove (34) for providing positioning to the inner surface of the base (10), and an auxiliary positioning hole (35). The embedded drug-can connecting seat (40) may be combined with the injection drug-can function and has a channel (41) to be connected to a replaceable drug-can container (42), or connected to an external drug-can connecting seat (44), which is fixed to and connected to the front sliding cover (11) of the housing, and connected to the an external drug-can container (8) (not shown in the drawing but will be described in detail later). In addition, the external drug-can container (8) may further be provided with an ultrasonic oscillation device for providing the pressuring effect. The drug-can connecting seat (40) includes a circular projection (401) to be fit into the auxiliary positioning hole (35) to prevent the rotation and displacement after combination, and a hole (402) to be combined with the drug-can container (42). The drug-can container (42) is a longitudinal sealed container having a front end formed with a diameter-reduced inserting portion (420) and the rear end formed with a fitting portion (422) with the uniform diameter, wherein an opening (421) penetrates through the body of the container from the front end to the rear end. The inserting portion (420) may be closed by a sheath when it is not used. When the inserting portion (420) is used, the opening (421) is aligned with the hole (402) and is thus connected to and communicated with the channel (41). The fitting portion (422) is embedded with a soft and slotted plug (423), and a gas communication tube (43) is correspondingly provided. The gas communication tube (43) has a tip portion (431) corresponding to the opening (421) of the fitting portion (422) of the drug-can container (42). The tip portion (431) can run through the plug (423) to form the communication. Also, a body of the gas communication tube (43) is formed with a transversal wing (432) and a longitudinal projection (433). The other end of the body and one end of the drug delivery pressuring tube (30) in the same direction penetrate through and are positioned in the substream gas hole (52) and the mainstream gas hole (51) of the fixed connection seat (50) are then coupled to mainstream and substream gas pressures (70, 71) (not shown in the drawing) provided by a control source (7) to be described later, so that the dual effect of quantitative gas delivery and drug pressuring and atomizing injection can be obtained. Also, the top of the substream gas hole (52) has a notch (521) to allow the longitudinal projection (433) to move and prevent the gas communication tube (43) from rotating. Projecting jointing portions (53) are respectively disposed on two sides of the notch (521). When the fixed connection seat (50) is connected to the base (10), the jointing portions (53) may be correspondingly and respectively stacked on the corresponding lugs (100) on the inner surface of the base (10), and screws may penetrate through the jointing portions (53) to screw the jointing portions (53) to the lugs (100). Similarly, the rear mounting seat (60) is also provided with a through hole (61), into which the mainstream gas pressure (70) may be conveniently inputted, and a V-shaped jointing portion (62), into which the substream gas pressure (71) may be conveniently inputted. Screw holes (63) are formed on the periphery of the rear mounting seat (60) so that screws may penetrate through the rear mounting seat (60) to screw the rear mounting seat (60) to the fixed connection seat (50).

Figure 2:
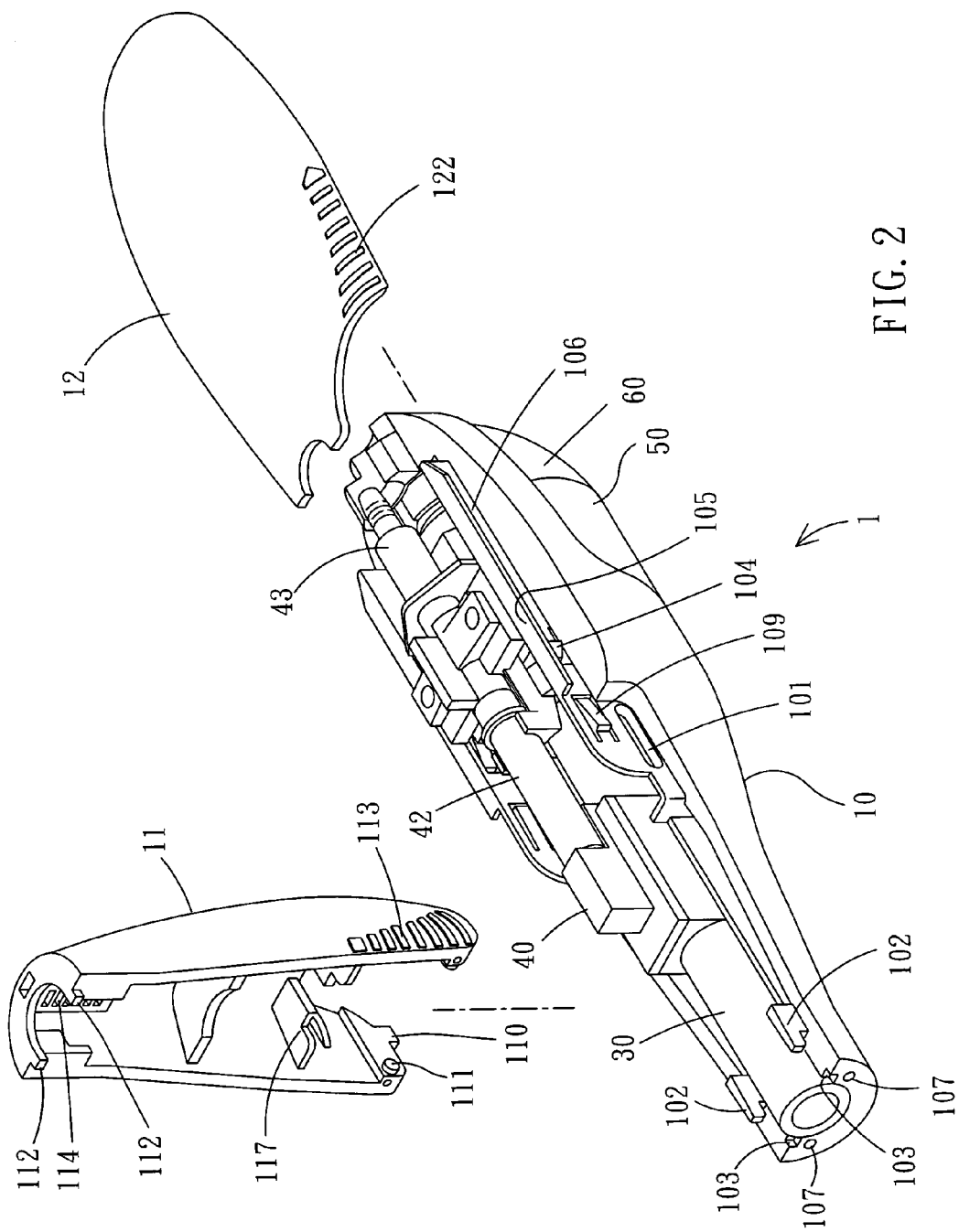
FIG. 2 is a schematically assembled illustration showing the drug delivery device according to the preferred embodiment of the invention.

FIG. 2 shows the assembled structure of the drug delivery device according to the preferred embodiment of the invention. In the base (10), the drug delivery pressuring tube (30), the embedded drug-can connecting seat (40), the drug-can container (42) and the gas communication tube (43) are successively placed and combined. One end of the base (10) is connected to the fixed connection seat (50) and the rear mounting seat (60). Finally, the front sliding cover (11) and the rear sliding cover (12) are combined with the base (10). The combination of the front sliding cover (11) and the base (10) will be described in the following. Opposite longitudinal slots (101) and elastic hooks (109) are formed on the middle sections of two sidewalls of the chamber of the base (10) chamber. Hooks (102) are formed near the front end of the base (10), and depressions (103) are formed on the edge of the base (10). One end of the front sliding cover (11) has an opening, and opposite engaging portions (110) and circle posts (111) are formed on two sides of the opening. One side of the engaging portion (110) is a straight side and may be hooked by the elastic hook (109) to prevent the movement.

The other side of the engaging portion (110) is formed with a small protrusion for positioning the lifted front sliding cover (11) to prevent the front sliding cover (11) from being over-rotated to cause the scratches of other elements. The circle post (111) may be embedded into the longitudinal slot (101) and slide therein. The other edge of the front sliding cover (11) is formed with opposite protrusions (112). When the front sliding cover (11) is combined with the base (10) and slides for positioning, the protrusion (112) may match with the depression (103). In addition, slip-resistant embosses (113) are formed on the proper locations of the outer circumferential surface of the front sliding cover (11) so that the front sliding cover (11) may be forced to open and slide. Also, the inner wall surface of the front sliding cover (11) is formed with opposite base posts (117) with semi-circular arc surfaces. The predetermined distance between the two base posts (117) only can allow the drug delivery pressuring tube (30) having the predetermined width to pass, so that the embedded drug delivery pressuring tube (30) may be effectively secured. Meanwhile, the opposite surfaces thereof are the semi-circular arc surfaces so that the surface scratches on the drug delivery pressuring tube (30) may be reduced when the front sliding cover (11) is opened. The combination of the rear sliding cover (12) and the base (10) will be described in the following. Opposite locks (104) are formed on the middle sections of the two sidewalls of the chamber of the base (10), and tabs (105) are extended toward the rear end above the locks (104), and sliding slots (106) are naturally formed below the tabs (105). The inner surface of the rear sliding cover (12) is projectingly formed with opposite hooking portions (121). When the rear sliding cover (12) is combined with the base (10), the two opposite hooking portions (121) slides in the sliding slots (106) to hook the locks (104) and thus combined and positioned. Similarly, slip-resistant embosses (122) are formed on the proper locations of the outer circumferential surface of the rear sliding cover (12) so that the rear sliding cover (12) may be forced to open, close and slide.

Figure 3:
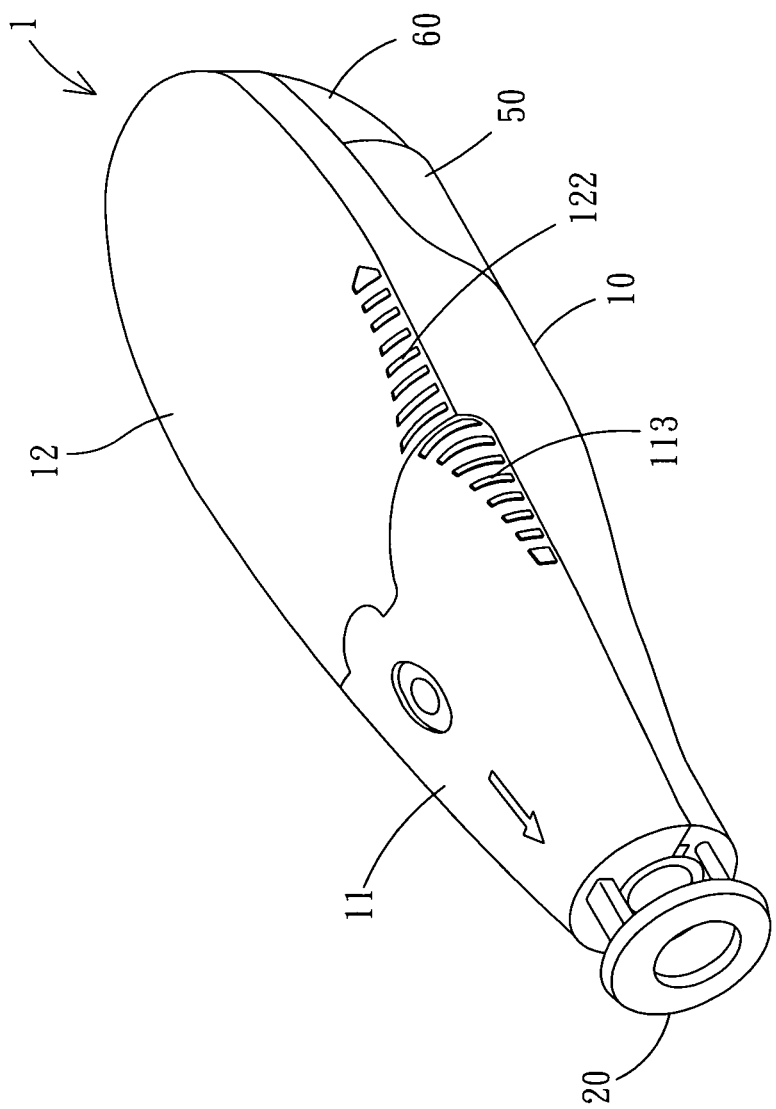
FIG. 3 is an overall exterior view showing the drug delivery device according to the preferred embodiment of the invention.

As shown in FIG. 3, according to the above-mentioned units, a complete, light and handy replaceable drug-can and quantitatively controlled drug delivery device can be constituted.

Figure 4:
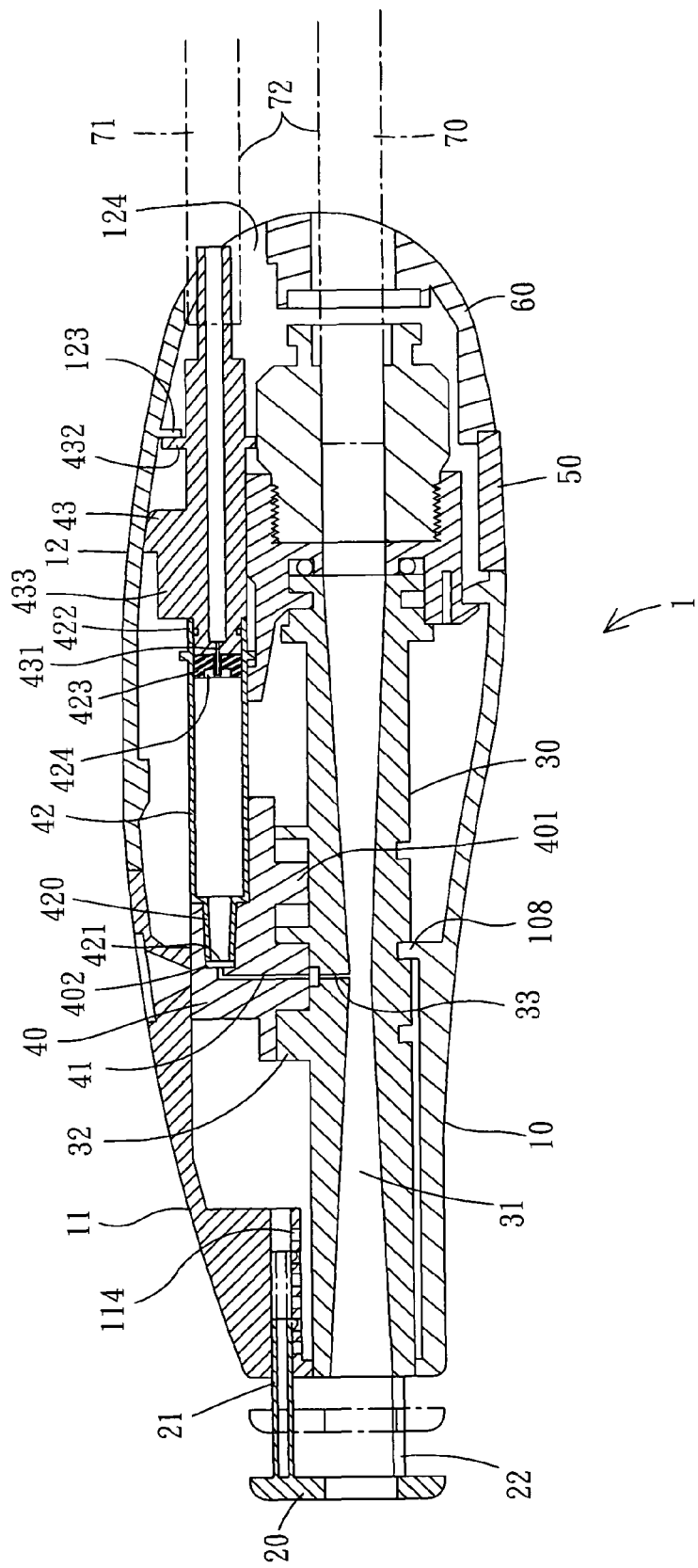
FIG. 4 is a cross-sectional view showing a drug delivery device according to the preferred embodiment of the invention.

FIG. 4 is a cross-sectional view showing the whole drug delivery device of the invention. As shown in FIG. 4, the drug delivery device (1) is embedded into the rib (108) on the inner surface of the base (10) through the positioning groove (34) on the bottom surface and is thus positioned. One end thereof is connected the adjustment seat (20). In practice, a hole seat (114) is formed on the edge of the front sliding cover (11) and extends inwardly by a distance, and through holes (107) are formed on the edge surface of the base (10). The adjustment seat (20) is in the form of a triangular insert, and has equally spaced elastic hooks (21) and inserting rods (22). The elastic hook (21) may be inserted into the corresponding hole seat (114). The inserting rod (22) is inserted into the correspondingly through hole (107). Thus, when the adjustment seat (20) and the base (10) are combined, the elastic hook (21) of the adjustment seat (20) can be inserted into the hole seat (114) and a suitable hole may be selected and hooked for positioning so that the gap between the adjustment seat (20) and the base (10) can be adjusted. Also, the other end of the drug delivery device (1) is coupled to the substream gas pressure (71) through the gas communication tube (43) to provide the quantitative gas delivery function, and the drug delivery pressuring tube (30) is coupled to the mainstream gas pressure (70) to provide the function of pressuring and jetting the drug and atomizing and injecting the drug.

Figure 5:
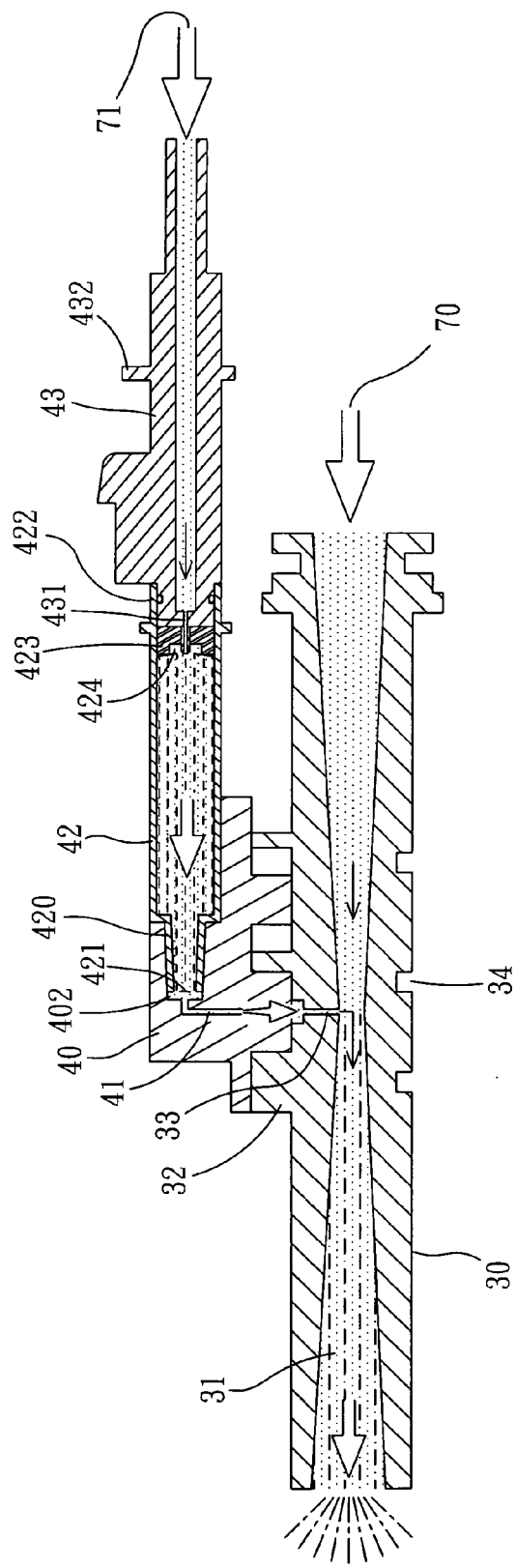
FIG. 5 is a schematic illustration showing the internal delivery of the drug delivery device according to the preferred embodiment of the invention.

FIG. 5 is a schematic illustration showing the internal delivery of the drug delivery device according to the preferred embodiment of the invention. As shown in FIG. 5, the mainstream and substream gas pressures (70, 71), controlled by the control source (7), are respectively coupled to the drug delivery pressuring tube (30) and the gas communication tube (43). The substream gas pressure (71) enters the drug-can container (42) through the gas communication tube (43) to push the drug to deliver slowly. Because a depressuring chamber is formed by thin slots in the gas communication tube (43) and shrunk openings (preferably having the diameter of 0.3 mm) are formed at the inlet and outlet, it is sufficient to control the minor pneumatic quantitative delivery function (the drug displacement may be reduced to be lower than 1 μl according to this design). The drug is outputted to the opening (421) of the inserting portion (420) on the other end of the drug-can container (42) through the fitting portion (422) on one end of the drug-can container (42) and through the plug (423), and then enters the micro and thin channel (41) of the embedded drug-can connecting seat (40) through the hole (402), and is then inputted into the drug delivery pressuring tube (30). The mainstream gas pressure (70) connected to one end of the drug delivery pressuring tube (30) pressures and jets the inputted drug and then outputs the drug from the other end of the drug delivery pressuring tube (30) in an atomized manner (this is the known Venturi tube principle, so detailed descriptions thereof will be omitted).

Figure 6:
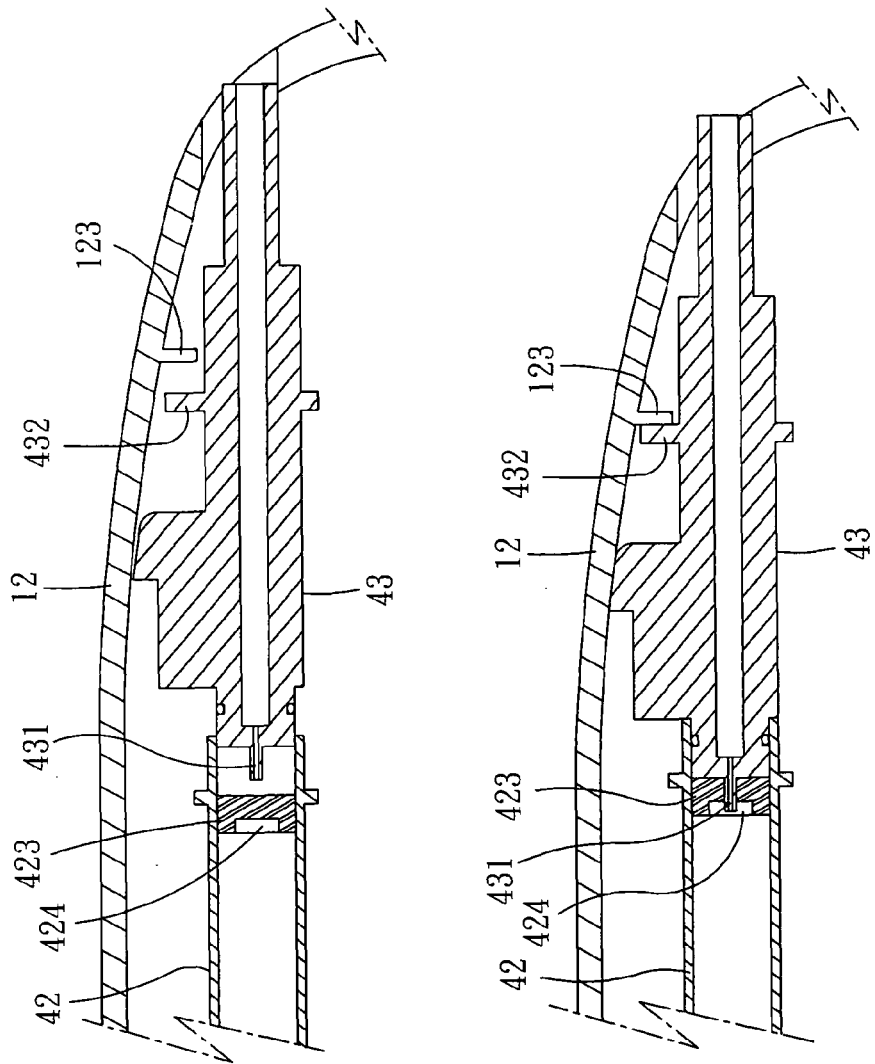
FIG. 6 is a schematic illustration showing the assembling of the replaceable drug-can container in the drug delivery device according to the preferred embodiment of the invention.

FIG. 6 is a schematic illustration showing the assembling of the replaceable drug-can container in the drug delivery device according to the preferred embodiment of the invention. As shown in FIG. 6, the opening (421) of the inserting portion (420) on one end of the drug-can container (42) is connected to the hole (402) of the embedded drug-can connecting seat (40) to form the communication, and the opening (421) of the fitting portion (422) on the other end thereof is connected to the gas communication tube (43). Because the fitting portion (422) of the drug-can container (42) has the soft plug (423), the tip portion (431) on one end of the gas communication tube (43) may run through the plug (423). At this time, the internal chambers still cannot communicate with each other. When the rear sliding cover (12) is assembled, the notch (124) at the distal end of the rear sliding cover (12) can allow the gas communication tube (43) to move, and the stopper (123) projectingly formed on its inner surface pushes the upper edge of the transversal wing (432) of the gas communication tube (43), so that the overall gas communication tube (43) further moves in the direction toward the drug-can container (42), and the tip portion (431) can completely run through the plug (423) to form the internal communication.

Figure 7:
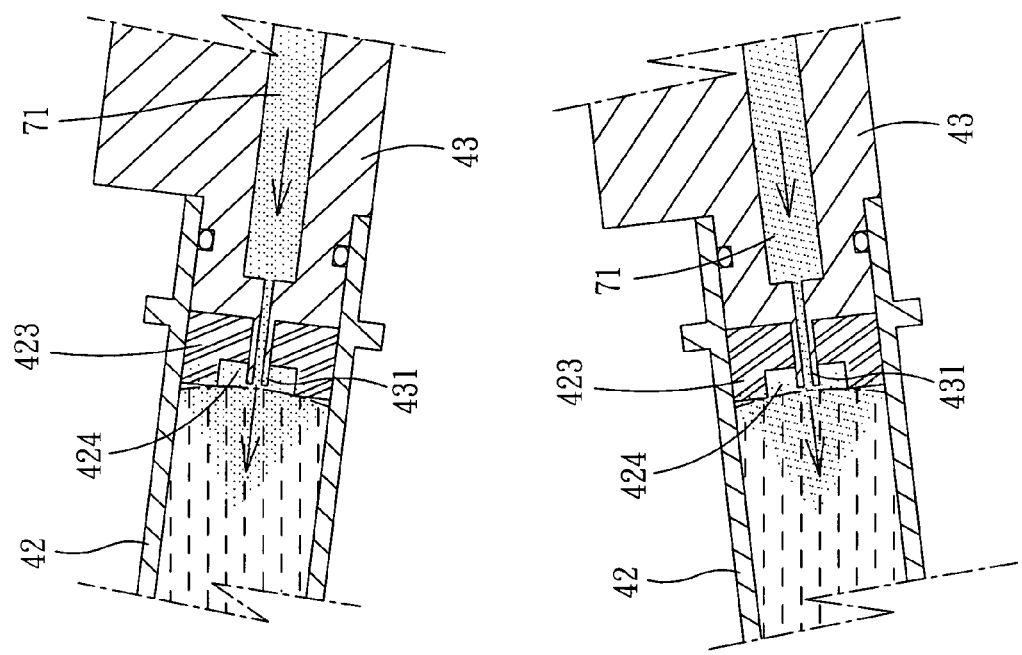
FIG. 7 is a partially schematic illustration showing the drug pushed by the gas when the gas communication tube is connected to the drug-can container in the drug delivery device according to the preferred embodiment of the invention.

FIG. 7 is a partially schematic illustration showing the drug pushed by the gas when the gas communication tube is connected to the drug-can container in the drug delivery device according to the preferred embodiment of the invention. As shown in FIG. 7, when the drug-can container (42) is connected to the gas communication tube (43), the tip portion (431) runs through the plug (423). When the substream gas pressure (71) continuously pushes the drug delivery, the residual drug is formed around the tip portion (431) penetrating through the plug (423). If the default injection is the quantitative injection, the residual drug may cause the insufficient drug. To solve this problem, the center of the surface of the plug (423) directed toward the inside of the tube is formed with a swallow slot (424) to reduce the residual drug according to the liquid surface tension (cohesive force). In addition, the drug-can container (42), the plug (423) and its swallow slot (424) may be integrally formed so that the manufacturing processes may be simplified.

Figure 8:
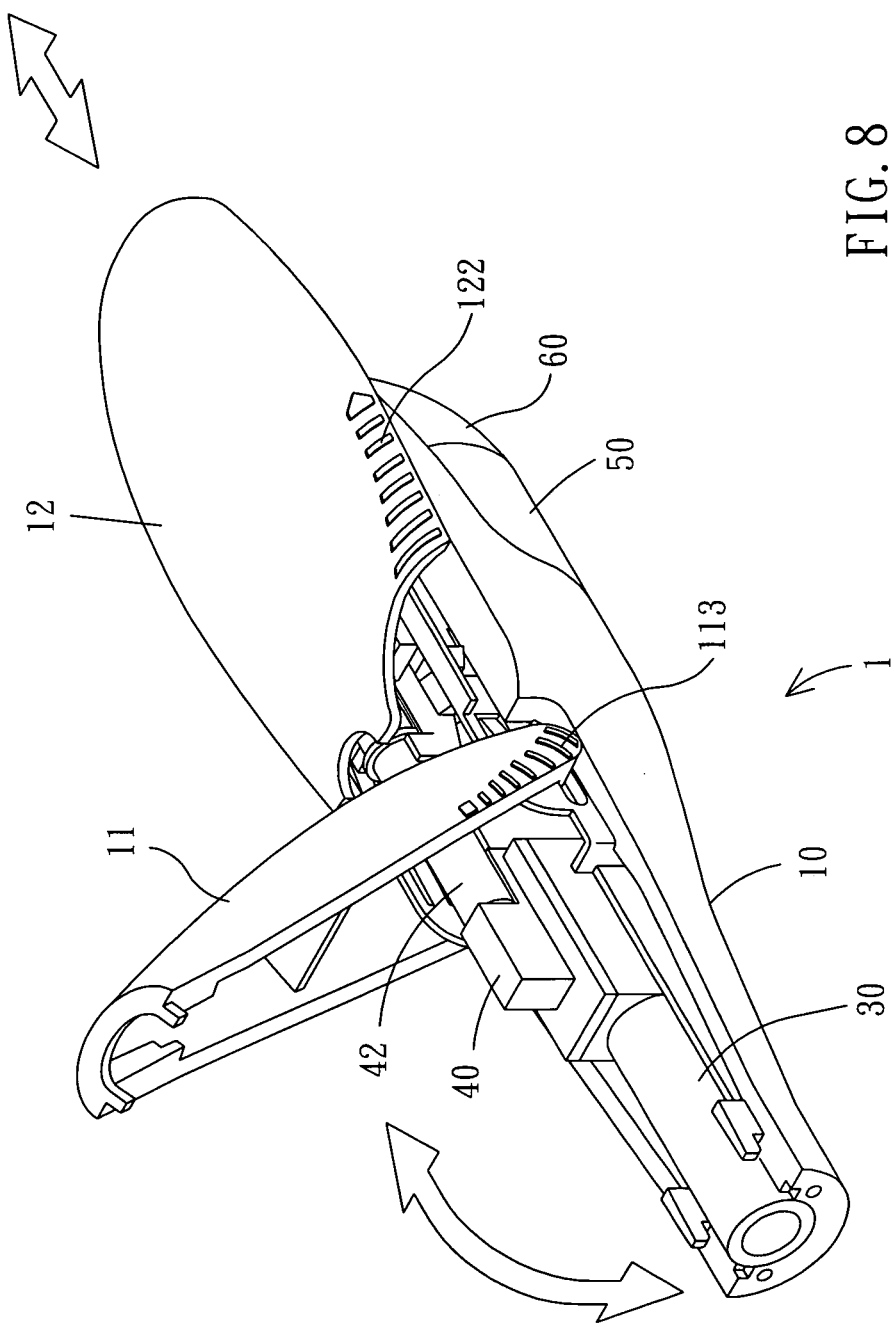
FIG. 8 is a schematically pictorial view showing the movements of the front and rear sliding covers in the drug delivery device according to the preferred embodiment of the invention.
Figure 9:
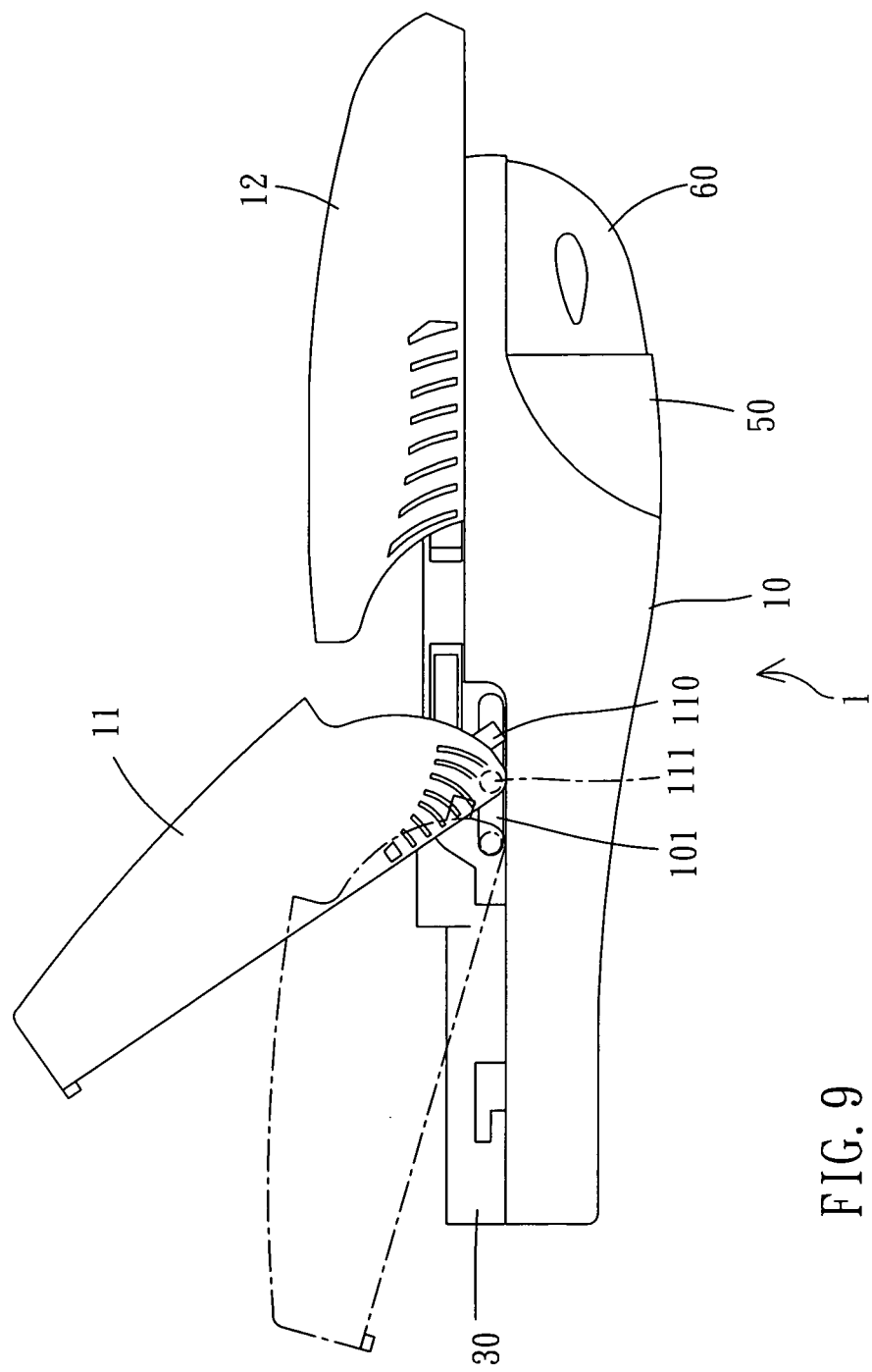
FIG. 9 is a schematically plane view showing the movements of the front and rear sliding covers in the drug delivery device according to the preferred embodiment of the invention.

FIGS. 8 and 9 are respectively schematically pictorial and plane views showing the movements of the front and rear sliding covers in the drug delivery device according to the preferred embodiment of the invention. As shown in FIGS. 8 and 9, the front sliding cover (11) can be rotated to open and close, and the rear sliding cover (12) can slide to open and close. This action is advantageous to the replacement of the drug-can container (42) or the disassembly of the drug delivery pressuring tube (30), or even the disassembly and cleaning of the overall set of units. Because the units are combined together, the units can be conveniently replaced, disassembled and cleaned. In addition, the units are reusable after disinfection, so that the cost is reduced.

Figure 10:
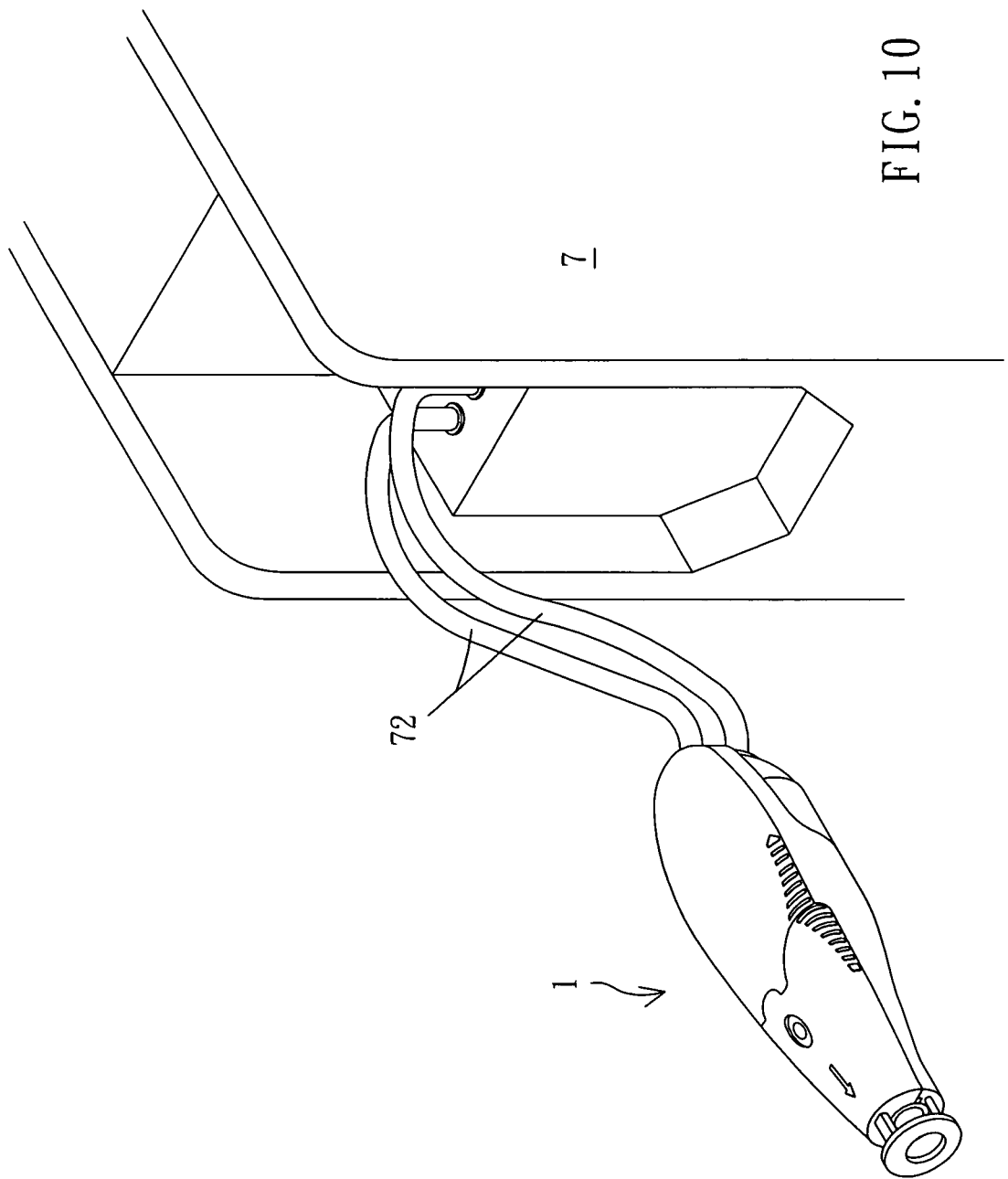
FIG. 10 shows a gas control source connected to the drug delivery device according to the preferred embodiment of the invention.

FIG. 10 shows a gas control source connected to the drug delivery device according to the preferred embodiment of the invention. As shown in FIG. 10, the control source (7) provides the mainstream gas pressure (70) and the substream gas pressure (71) and functions to adjust and control the pressures of the mainstream and substream gas pressures (70, 71), the time, and the output time difference therebetween. In practice, conduits (72) connect the drug delivery device (1) to the control source (7). The gas used in the control source (7) of the invention is externally inputted, and a proportional valve is utilized to perform the automatic pressure control to get rid of the trouble of the manual adjustment. The gas may be generated by a high-pressure inert gas cylinder, and a pressure accumulation tank device is also provided. In this example, the operation pressure of the mainstream gas pressure (70) ranges from 5 $kg/cm^2$ to 12 $kg/cm^2$, and the operation pressure, and the substream gas pressure (71) controlled by the proportional valve ranges from 0.02 $kg/cm^2$ to 0.1 $kg/cm^2$.

Figure 11:
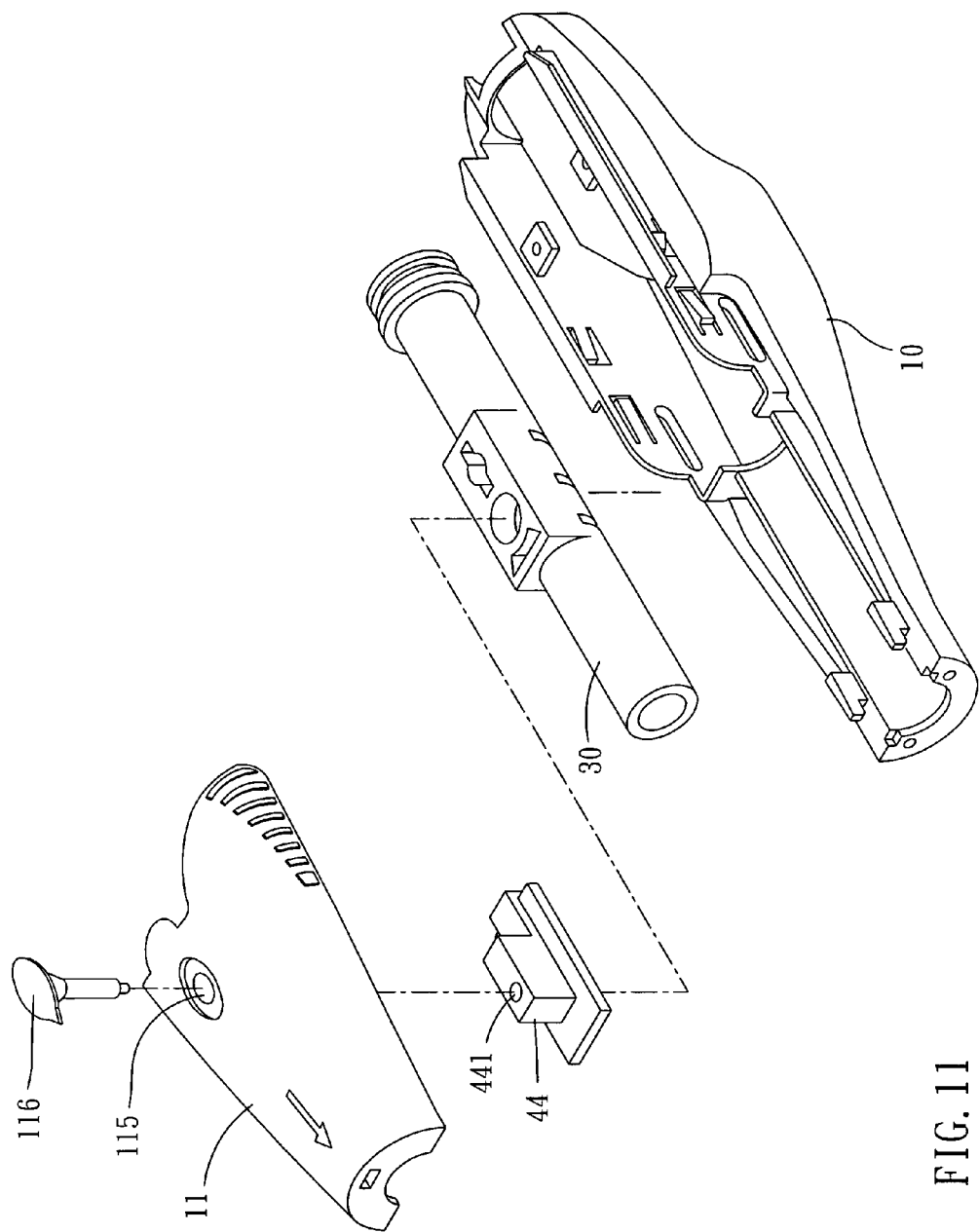
FIG. 11 is an exploded view showing a drug delivery device according to the other preferred embodiment of the invention.
Figure 12:
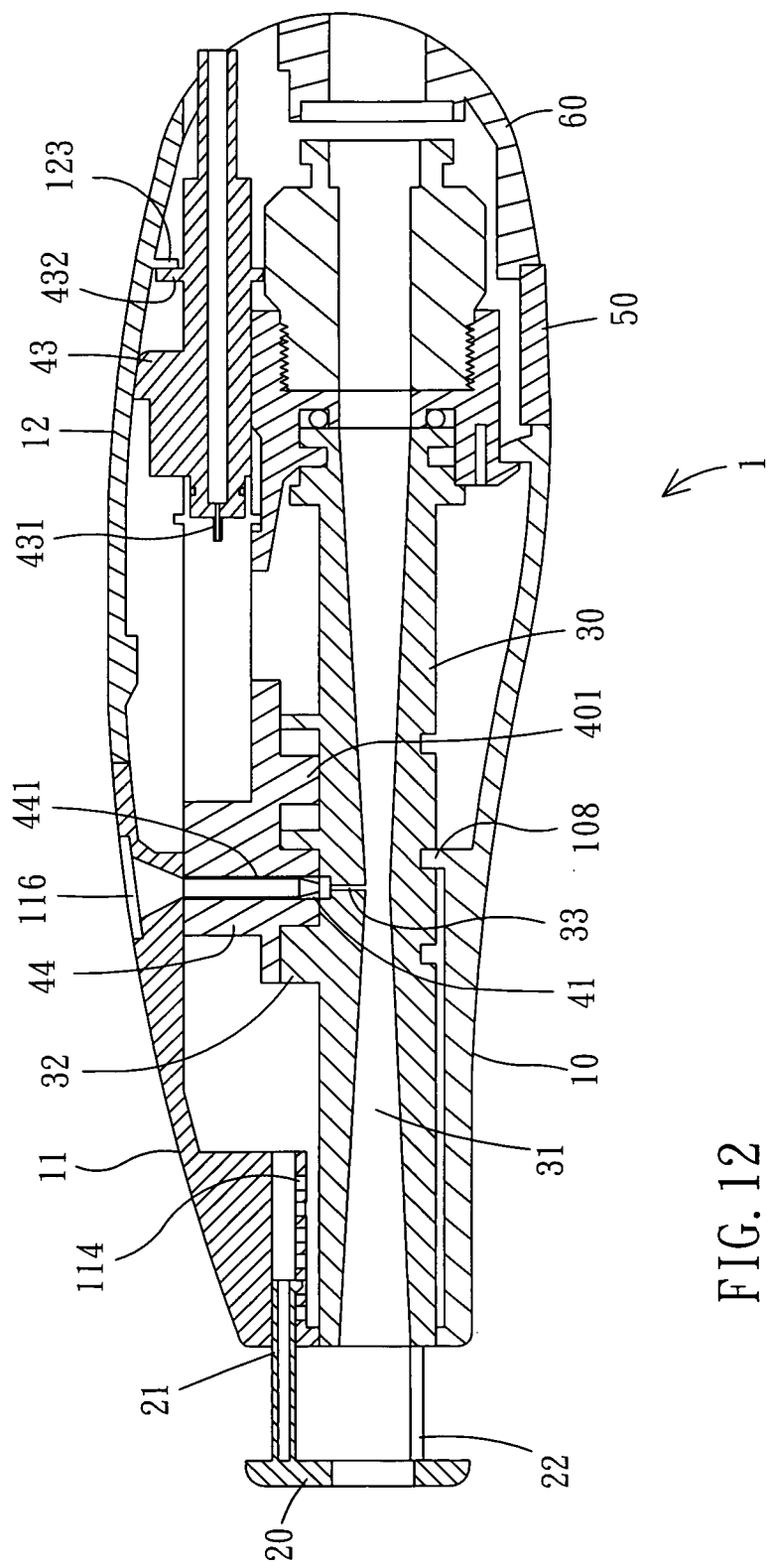
FIG. 12 is a cross-sectional view showing the drug delivery device according to the other preferred embodiment of the invention.

FIG. 11 is an exploded view showing a drug delivery device according to the other preferred embodiment of the invention. FIG. 12 is a cross-sectional view showing the drug delivery device according to the other preferred embodiment of the invention. The difference between the drug delivery device (1) of the two embodiments is that the external drug is directly inputted in this embodiment. In manufacturing, the drug delivery device (1) includes the housing, the adjustment seat (20), the drug delivery pressuring tube (30), the fixed connection seat (50) and the rear mounting seat (60), which are the same as those of the previous embodiment. The different unit structure is the external drug-can connecting seat (44), which has a through hole (441) directly penetrating through the drug-can connecting seat (44) from the outside. Meanwhile, a connection hole (115) corresponding to the through hole (441) is formed on the front sliding cover (11) so that the external drug input may be connected to the connection hole (115) via the conduit (72). Also, a pin (116) for closing the connection hole (115) when the external drug supply input is not used is also provided.

Figure 13:
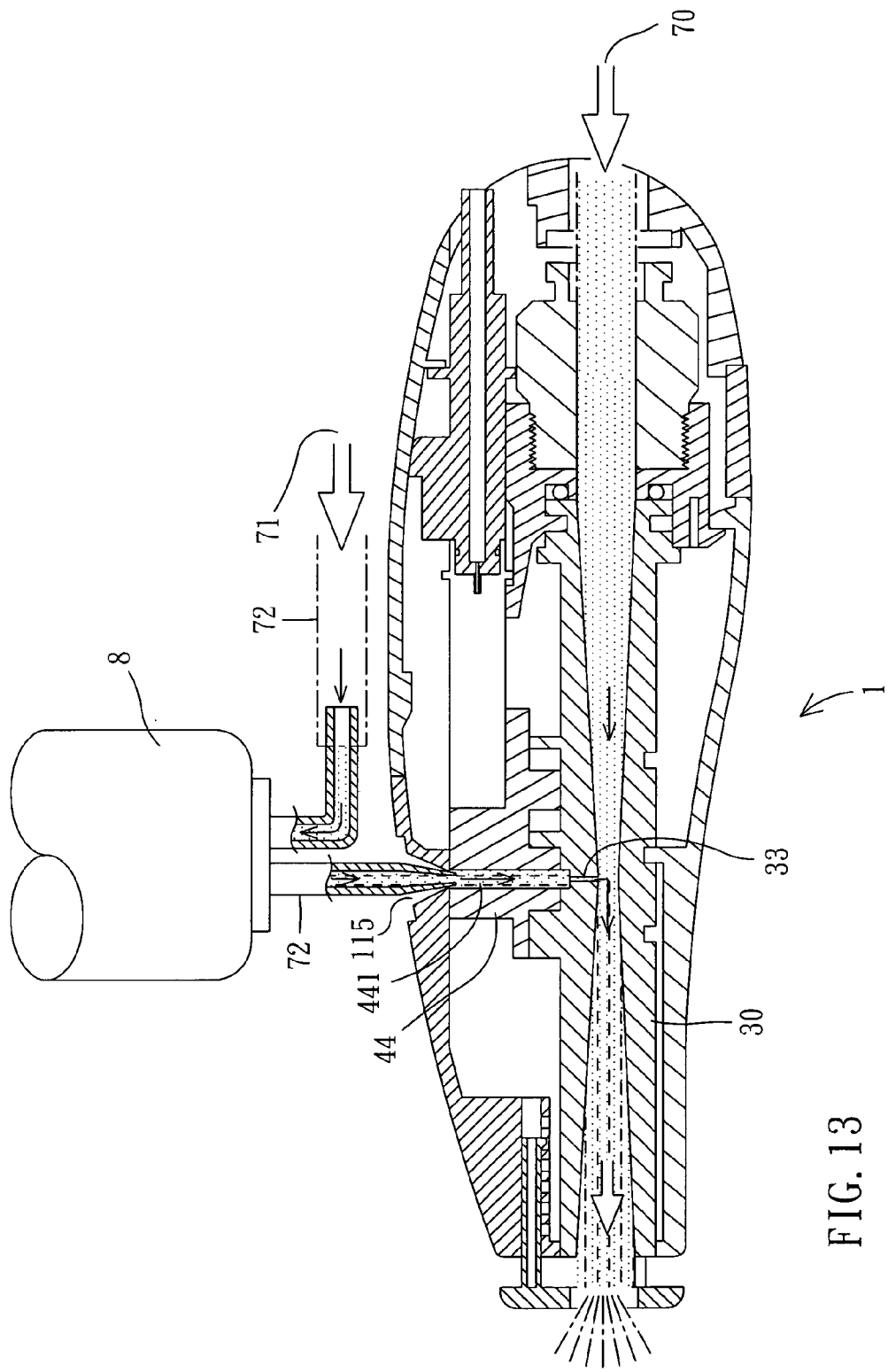
FIG. 13 is a schematic illustration showing the actual implementation of the drug delivery device according to the other preferred embodiment of the invention.

FIG. 13 is a schematic illustration showing the actual implementation of the drug delivery device according to the other preferred embodiment of the invention. As shown in FIG. 13, the external drug-can container (8) is used in conjunction with the drug delivery device (1) in this embodiment. In practice, the external drug-can container (8) has one port connected to the conduit (72) for injecting the substream gas pressure (71), and the other port connected to the other conduit (72), which is connected to the external drug-can connecting seat (44) through the connection hole (115) on the front sliding cover (11). The through hole (441) and the thin channel (33) of the drug delivery pressuring tube (30) are adopted to form the communicated state so that the external drug may be inputted into the drug delivery device (1) conveniently. In addition, the drug delivery pressuring tube (30) is coupled to the pressuring and jetting actions provided by the mainstream gas pressure (70) so that the drug is injected in an atomized manner. Furthermore, an ultrasonic oscillation device is further disposed inside the external drug-can container (8) so that the outputted drug may become finer in an atomized manner.

In summary, the invention includes the following advantages.

First, the assembling type drug-can connecting seat makes it possible to disassemble and assemble the drug-can container and the drug delivery pressuring tube freely.

Second, the internal or external drug-can container can be easily replaced, and the replaceable connecting seat is provided.

Third, the assembled structure of the drug-can container has the ultrasonic oscillation device with the atomizing function.

Fourth, the gas communication tube has the depressuring function.

Fifth, the structure for using the gas to push the drug-can container is designed according to the liquid surface tension (cohesive force) property.

In summary, the drug delivery device of the invention has the advantages mentioned hereinabove, and can achieve the predicted objects and effects.

New characteristics and advantages of the invention covered by this document have been set forth in the foregoing description. It is to be expressly understood, however, that the drawings are for the purpose of illustration only and are not intended as a definition of the limits of the invention. Changes in methods, shapes, structures or devices may be made in details without exceeding the scope of the invention by those who are skilled in the art. The scope of the invention is, of course, defined in the language in which the appended claims are expressed.

What is claimed is:

1. A drug delivery device (1), comprising:
  a housing, comprising:
    a base (10), having an accommodating space, wherein a rib (108) is formed on a bottom surface of the accommodating space, and two longitudinal slots (101), two elastic hooks (109), two locks (104) being disposed on the middle section of two inner sidewalls of the accommodating space; moreover, each of the locks (104) being provided with a tab (105) thereon, and the tab (105) is formed with two sliding slots (106) thereunder;
    a front sliding cover (11), having two engaging portions (110) and two circle posts (111) on two inner sidewalls of a rear opening thereof; wherein the two circle posts (111) are respectively embedded into the two longitudinal slots (101) of the base (10), such that the front sliding cover (11) connected to the base (10) is able to cover the base (10) slidably; moreover, the front sliding cover (11) is connected to the base (10) by the two elastic hooks (109) being hooked on the two engaging portions (110); and
    a rear sliding cover (12), having two hooking portions (121) on two inner sidewalls thereof, wherein the rear sliding cover (12) is connected to the base (10) by the two hooking portions (121), and the rear sliding cover (12) being able to slidably cover the base (10) when the two hooking portions (121) sliding on the two sliding slots (106) and then hooked on the two locks (104);
  a drug delivery pressuring tube (30), being disposed in the accommodating space of the base (10), and comprising:

an inner hole (31), being formed in the drug delivery pressuring tube (30) and a diameter-reduced channel is formed from the inner hole (31) to the center of the drug delivery pressuring tube (30);

a connection portion (32), being disposed on the middle section of the outer circumferential surface of the drug delivery pressuring tube (30), and having a penetrated channel (33) for communicating with the inner hole (31); and a positioning groove (34), being disposed on the outer surface of the bottom of the drug delivery pressuring tube (30) for combining with the rib (108), such that the drug delivery pressuring tube (30) would be fixed onto the bottom surface of the accommodating space of the base (10);

a connecting seat (40), having a hole (402) and a channel (41) for making the connecting seat (40) be disposed on the drug delivery pressuring tube (30), so as to combine with the connection portion (32) of the drug delivery pressuring tube (30);

a drug container (42), being formed with a diameter-reduced inserting portion (420) on the front end thereof, wherein the drug container (42) is combined with the connecting seat (40) by inserting the diameter-reduced inserting portion (420) into the hole (402) and connecting the diameter-reduced inserting portion (420) to the channel (41); moreover, the drug container (42) further comprising a fitting portion (422) on the rear end thereof, and a slotted plug (423) is disposed in the fitting portion (422);

a gas communication tube (43), having a tip portion (431) for being penetrated through the slotted plug (423) of the drug container (42);

a fixed connection seat (50), having a primary-stream gas hole (51) and secondary-stream gas hole (52), wherein the secondary-stream gas hole (52) is connected to the rear end of the gas communication tube (43);

a rear-mount seat (60), having a through hole 61, wherein the rear-mount seat (60) is combined with the fixed connection seat (50) through the through hole (61) being combined with the primary-stream gas hole (51); and an adjustment seat (20), being combined with the front end of the housing constituted by the base (10), the front sliding cover (11) and the rear sliding cover (12), wherein the adjustment seat (20) is a triangular inserting member, and the gap between the adjustment seat (20) and the housing is adjustable;

wherein the primary-stream gas hole (51) and the secondary-stream gas hole (52) are respectively connected to two conduits (72), such that a drug in the drug container (42) can be atomized through a primary-stream gas pressure (70) and a secondary-stream gas pressure (71) delivered by using the two conduits (72); such that the drug would be entered into the inner hole (31) of the drug delivery pressuring tube (30) through the hole (402) and the channel (41) by the driving force of the secondary-stream gas pressure (71), and then quantitatively ejected from The drug delivery device (1) in an atomization form by the driving force of the primary-stream gas pressure (70).

2. The drug delivery device (1) of claim 1, wherein the base (10) further has:

two depressions (103), being oppositely formed on the edge of the front end of the accommodating space;

two through holes (107), being formed on the end-face of the front end of the base (10); and two lugs (100), being formed on the inner surface of the accommodating space and opposite to each other, wherein the lug (100) is adjacent to the sliding slot (106).

3. The drug delivery device (1) of claim 2, wherein the front sliding cover (11) further has:

two protrusions (112), being oppositely formed on both sides of the opening of the front sliding cover (11) for matching the two depressions (103) when the base (10) is covered with the front sliding cover (11);

a hole seat (114), being disposed on the inner surface of the front end of the front sliding cover (11);

two base posts (117), being oppositely disposed on inner surface of the front sliding cover (11) for locating the drug delivery tube (30) when the drug delivery tube (30) is disposed in the accommodating space of the base (10); and a slip-resistant emboss (113), being formed on the outer surface of the front sliding cover (11).

4. The drug delivery device (1) of claim 2, wherein a transversal wing (432) and a longitudinal protrusion (433) are formed on the gas communication tube (43).

5. The drug delivery device (1) of claim 4, wherein the rear sliding cover (12) further has:

a notch (124), being formed on the rear end of the rear sliding cover (12) for allowing the gas communication tube (43) to be moved;

a slip-resistance emboss (122), being formed on the outer surface of the rear sliding cover (12); and a stopper (123), being formed on the inner surface of the rear sliding cover (12), for pushing the transversal wing (432) when the tip portion (431) is penetrated through the slotted plug (423), such that the plug (423) would be completely run through.

6. The drug delivery device (1) of claim 1, wherein the drug delivery tube (30) further comprises an auxiliary positioning hole (35) adjacent to the connection portion (32).

7. The drug delivery device (1) of claim 6, wherein a circular protrusion (401) is disposed on the bottom of the connecting seat (40) for being inserted into the auxiliary positioning hole (35) of the drug delivery pressuring tube (30).

8. The drug delivery device (1) of claim 3, wherein the adjustment seat (20) has at least one elastic hook (21) for being correspondingly inserted into the hole seat (114) of the front sliding cover (11) and at least one inserting rod (22) for being correspondingly inserted into the through hole (107) of the base (10); such that the gap between the adjustment seat (20) and the housing would be adjusted by the disposing of the elastic hook (21) being inserted into the hole seat (114).

9. The drug delivery device (1) of claim 4, wherein the fixed connection seat (50) further has:

a notch (521), being formed on the secondary-stream gas hole (52) for allowing the longitudinal protrusion (433) to be moved, and preventing the gas communication tube (43) from being rotated; and two joining portions (53), being respectively disposed on both sides of the notch (521), wherein when the fixed connection seat (50) is connected to the base (10), the two joining portion (53) would be correspondingly and respectively fixed on the two lugs (100) of the base (10).

10. The drug delivery device (1) of claim 4, wherein the rear-mount seat (60) further has:

a V-shaped joining portion (62), being formed on the through hole (61) for providing the secondary-stream gas pressure (71) to be conveniently inputted; and two screw holes (63), being formed on the periphery of the rear-mount seat (60), and used for facilitating the rear-mount seat (60) be fixed on the connection seat (50).

11. The drug delivery device (1) of claim 1, wherein the primary-stream gas pressure (70) is ranged from 5 kg/cm2 to 12 kg/cm2, and the secondary-stream gas pressure (71) is ranged from 0.02 kg/cm2 to 0.1 kg/cm2.

12. The drug delivery device (1) of claim 1, wherein a shallow slot (424) is formed on the surface of the plug (423) for reducing the residual amount of the drug by way of surface tension.

13. The drug delivery device (1) of claim 1, wherein a pressure-reducing chamber is formed by a thin slot in the gas communication tube (43), and two diameter-reduced openings are formed at the inlet and outlet of the of the gas communication tube (43).

\* \* \* \* \*